United States Patent [19]

Garabedian

[11] Patent Number: Plant 5,609

[45] Date of Patent: Dec. 24, 1985

[54] PLUM TREE, "WESTERNER"

[76] Inventor: John M. Garabedian, P.O. Box 7883, Fresno, Calif. 93747

[21] Appl. No.: 580,196

[22] Filed: Feb. 15, 1984

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A new and distinct variety of plum tree which is somewhat similar to the Laroda Plum Tree (unpatented), concurrently with which it bears fruit which is characteristically larger in size, deeper and fuller in external color and possesses a substantially greater amount of red coloration in its flesh.

1 Drawing Figure

BACKGROUND OF THE NEW VARIETY

The present invention relates to a plum tree, known as the "WESTERNER", and more particularly to a plum tree which bears fruit at substantially the same time as the Laroda Plum Tree (unpatented) but which fruit is distinguished from that of the Laroda Plum Tree in being of larger size, having a deeper and more extensive skin color, and in having a substantially greater amount of red color in its flesh.

For many years, the applicant has grown large acreages of fruit trees and has constantly sought to produce improved fruit trees. This quest has involved several procedures. First, he has constantly kept his orchards under surveillance in an effort to find and reproduce any sports or mutations that might occur and promise improved quality or characteristics. Second, he has germinated thousands of random pollinated seedlings, grown them to maturity and evaluated the resultant trees and their fruit. Third, he has cross-pollinated selected varieties and similarly evaluated the resultant progeny. Whether a random pollinated seedling, a cross-pollinated seedling, a sport or a mutation, he has asexually reproduced the trees of selected quality. The subject plum tree resulted from the germination of a random pollinated stone on the applicant's ranch near Church and Greenwood Avenues, near Sanger, Calif. in 1968. The seedling of the present variety was germinated by the applicant and grown with thousands of other seedlings on his ranch near the intersection of the designated Church and Greenwood Avenues until its unique qualities were detected and appreciated. The applicant then asexually reproduced the instant variety of plum tree by budding scions of the seedling into plum rootstock and grew the resultant trees in the applicant's plum orchard at the northwest corner of Belmont and Armstrong in Fresno, Calif. The budded progeny were grown at such intersection until it was determined that the new variety dependably and accurately reproduced the superior characteristics observed by the applicant in the original seedling.

The instant variety of plum tree has not been introduced to the trade. As will subsequently become apparent, it is somewhat similar to the Laroda Plum Tree (unpatented) with which it bears fruit which matures at substantially the same time. The Laroda and the present variety plum tree are harvested on or about July 15. The instant variety is distinguished from the Laroda Plum Tree in its production of fruit of larger size, deeper and more extensive external color, and brighter flesh coloration.

BRIEF DESCRIPTION OF THE DRAWING

The accompanying drawing is a color photograph of a characteristic twig bearing typical leaves, a cluster of four plums showing their external coloration sufficiently mature for harvesting and shipment, three mature plums of the color when matured on the trees, a plum halved transversely of the suture plane to illustrate the flesh coloration and five stones, all of the subject variety.

DETAILED DESCRIPTION

Referring more specifically to the pomoligical details of this new and distinct variety of plum tree, the following has been observed under the ecological conditions prevailing in the designated orchards near Sanger and Fresno, Calif. All major color code plate identifications are by reference to the *Dictionary of Color,* by A. Maerz and M. Paul, Second Edition, published in 1950.

TREE

Size: Medium, depending upon pruning practices.
Vigor: Vigorous.
Figure: Upright, spreading, dense, vase-formed.
Productivity: Productive.
Regularity of bearing: Regular.
Trunk:
- *Thickness.*—Medium.
- *Texture of bark.*—Medium, shaggy.

Branches:
- *Thickness.*—Medium.
- *Texture.*—Medium.
- *Color.*—Brown, Plate 8-J-10 (Folcon Muskrat +), striated longitudinally to Plate 12-G-8.
- *Lenticels.*—Numerous, medium in size.

Leaves:
- *Shoot.*—Size — Medium; length 10.31±1.14 cm; width 4.20±0.43 cm.
- *Form.*—Obovate, apex acuminate, acutely pointed.
- *Thickness.*—Medium.
- *Color.*—Dark green, upper surface Plate 23-L-11; lower surface Plate 22-E-7.
- *Texture.*—Nearly smooth, base acuminate.
- *Marginal form.*—Glandular crenate.
- *Petiole.*—Length — Long; Thickness — Medium to slender.

*Glands.*—Average number 2; usually alternate; small; globose, red-green; one or more positioned on apical portion of petiole.

*Stipules.*—Small, linear, acute, ephemeral.

Spur:

*Size.—Medium; length* 8.81±0.73 cm; width 2.90±0.22 cm.

*Form.*—Slightly obovate, apex acuminate.

*Thickness.*—Medium.

*Color.*—Dark Green, upper surface Plate 23-L-11; lower surface Plate 22-E-7.

*Texture.*—Nearly smooth, base acuminate.

Flower buds: Small, short, obtuse, conic, plump, appressed to free, glabrous.

Flowers: Medium to small, white, Anthers Yellow; date of first bloom — Feb. 23, 1983; date of full bloom — Mar. 6, 1983; late compared with other varieties.

FRUIT

Maturity when described: Hard ripe; date — July 15.

Size: Uniform large; axial diameter — 6.08±0.39 cm; diameter transverse in suture plane — 6.61±0.37 cm; diameter transverse in cheek plane — 6.66±0.34 cm.

Form: Uniform symmetrical, broadly ovate to globular.

*Suture.*—An inconspicuous color line, rarely a very shallow, narrow groove from base to apex, pistil point slightly depressed.

*Ventral surface.*—Rounded, lips equal.

*Cavity.*—Flaring, circular to acuminate, deep; depth — 1.23±0.25 cm; breadth — 2.46±0.27 cm; markings — none.

*Base.*—Rounded, occasionally slightly truncated.

*Apex.*—Slightly depressed.

*Pistil point.*—Apical, obscure.

Skin: Medium thickness; medium texture; slightly bitter; tenacious to flesh; no observed tendency to crack.

*Color.*—Dark red, essentially full colored, but ground color, Plate 12-K-5; blush color approximately Plate) 56-E-12 (Port).

*Down.*—Heavy, blue-gray, Plate 38-C-6.

*Dot.*—Small, scattered (not numerous), inconspicuous under bloom; lacking basally and on suture edge; most numerous apically.

Flesh:

*Color.*—Light creamy white, becoming red from skin to cavity with maturity; to full red when ripe; ground color Plate 9-D-1, mostly diffused red, especially from skin; to Plate 4-L-7; surface of pit cavity darker red.

*Fibers.*—Few, fine, tender.

*Ripening.*—Even.

*Flavor.*—Subacid to mild, flat.

*Aroma.*—Wanting.

*Eating quality.*—Fair.

Stone: Semifree; adheres to flesh along ventral edges; free on sides toward base; short fibers.

*Size.*—Medium; length 2.37±0.14 cm; breadth 2.03±0.10 cm; thickness 1.12±0.05 cm.

*Form.*—Broad oval.

*Base.*—Straight.

*Hilum.*—Broad, oblong.

*Apex.*—Rounded with short, blunt tip.

*Sides.*—Unequal, ventral longer.

*Surface.*—Irregularly ridged near base; finely rugose.

*Ventral edge.*—Thin, without wing throughout; lateral grooves variably often interrupted, broad, rather deep.

*Dorsal edge.*—Narrow with deep, narrow groove usually throughout, but occasionally closed medianly.

*Color.*—Light tan, Plate 9-C-3.

*Tendency to split.*—Slight.

Use: Dessert.

Keeping quality: Good.

Resistance to insects: Medium.

Resistance to disease: Medium.

Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is new and desired to be secured by Letters Patent is:

1. A new and distinct variety of plum tree substantially as illustrated and described which is somewhat similar to the Laroda Plum Tree (unpatented) with which it bears fruit which matures at substantially the same time but from which it is distinguished by bearing fruit of larger size, deeper and fuller external color, and a substantially greater amount of red color in its flesh.

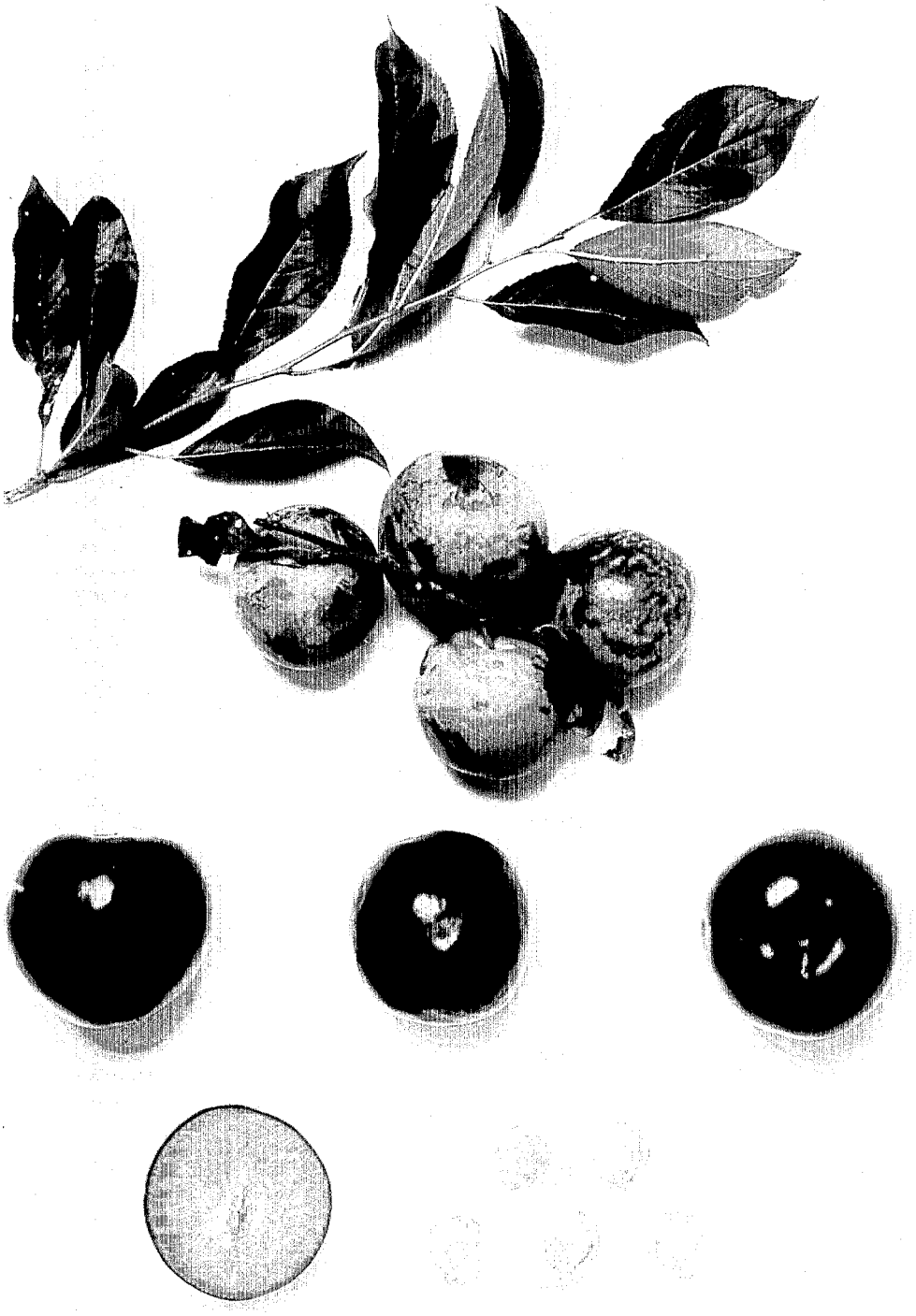

* * * * *